United States Patent [19]

Scouten

[11] Patent Number: 4,661,637
[45] Date of Patent: Apr. 28, 1987

[54] CONVERSION OF SOLID METAL PHENATES TO PHENOLS

[75] Inventor: Charles G. Scouten, Westfield, N.J.

[73] Assignee: Exxon Research and Engineering Company, Florham Park, N.J.

[21] Appl. No.: 808,024

[22] Filed: Dec. 12, 1985

Related U.S. Application Data

[72] Continuation in part of Ser. No. 757,908, Jul. 22, 1985, now U.S. Pat. No. 4,595,489, which is a Continuation of Ser. No. 452,956, Dec. 27, 1982, now abandoned.

[51] Int. Cl.$^4$ .............................................. C07C 39/04
[52] U.S. Cl. .................................................. 568/716
[58] Field of Search ................. 568/716, 806; 208/263

[56] References Cited

U.S. PATENT DOCUMENTS 1,245,343  11/1917  Howard .............................. 568/716
4,256,568  3/1981   Schloseberg ...................... 208/263
4,299,691  10/1981  Dougherty ........................ 208/263
4,595,489  6/1986   Scouten ............................. 208/263

OTHER PUBLICATIONS

Ges. Abhanl Kenninis Kohle, vol. 4, (1919) pp. 236-263.

Primary Examiner—Werren B. Lone
Attorney, Agent, or Firm—Henry E. Naylor

[57] ABSTRACT

Disclosed is a process for converting solid metal phenates to phenols and hydroxides of the metals of the phenates by treating the phenates with steam at a temperature from about 250° C. to about 450° C.

5 Claims, 2 Drawing Figures 4,661,637

CONVERSION OF SOLID METAL PHENATES TO PHENOLS

FIELD OF THE INVENTION

CROSS REFERENCE TO RELATED APPLICATIONS

This is a continuation-in-part application of U.S. 757,908 filed Jul. 22, 1985, which is a continuation of U.S. 452,956 filed Dec. 27, 1982, now abandoned.

The present invention relates to the conversion of solid metal phenates to phenols. The phenates are heated, at relatively low temperatures, in the presence of steam to recover the phenols and the hydroxide of the metal of the phenate.

It is known that metal phenates are produced when phenols are contacted with certain metal oxides or hydroxides. For example, U.S. Pat. No. 4,256,568, which is incorporated herein by reference, teaches that phenols, of a carbonaceous stream, react with these oxides and hydroxides resulting in the formation of metal phenates, which are easily separated from the purified stream. Further, it is taught in Ges. Abhandl. Kenninis Kohle, Vol. 4, pp. 237–63 (1919), that certain metal phenates, such as calcium phenoxide, can be heated in the presence of carbon dioxide to yield phenols and calcium carbonate.

Still another method is taught in U.S. Pat. No. 4,256,568, which method comprises treating a phenol-containing stream, such as a coal liquid, with a multivalent metal oxide and/or hydroxide. The resulting hydroxy metal phenate is then pyrolyzed to a temperature of about 650° C. to recover the phenols and an oxide of the multivalent metal.

Another method is disclosed in U.S. Pat. No. 4,299,691 which also employs a multivalent metal oxide and/or hydroxide for removal of phenols from phenol-containing hydrocarbonaceous streams. The resulting hydroxy metal phenates are then reacted with one or more $C_1$ to $C_{10}$ aliphatic alcohols or $C_7$ to $C_{16}$ aryl-alkyl primary alcohols.

SUMMARY OF THE INVENTION

In accordance with the present invention, phenols are recovered from solid metal phenates by treating the solid metal phenates with steam at a temperature from about 250° C. to about 450° C. thereby forming phenols and hydroxides of the metal of the phenate.

In preferred embodiments of the present invention, the metal of the phenate is an alkali or alkaline-earth metal.

In other preferred embodiments of the present invention, the metal is selected from the group consisting of sodium and potassium and the metal phenate is contacted with steam at a temperature of about 350° C.

DETAILED DESCRIPTION OF THE INVENTION

Figure 1:
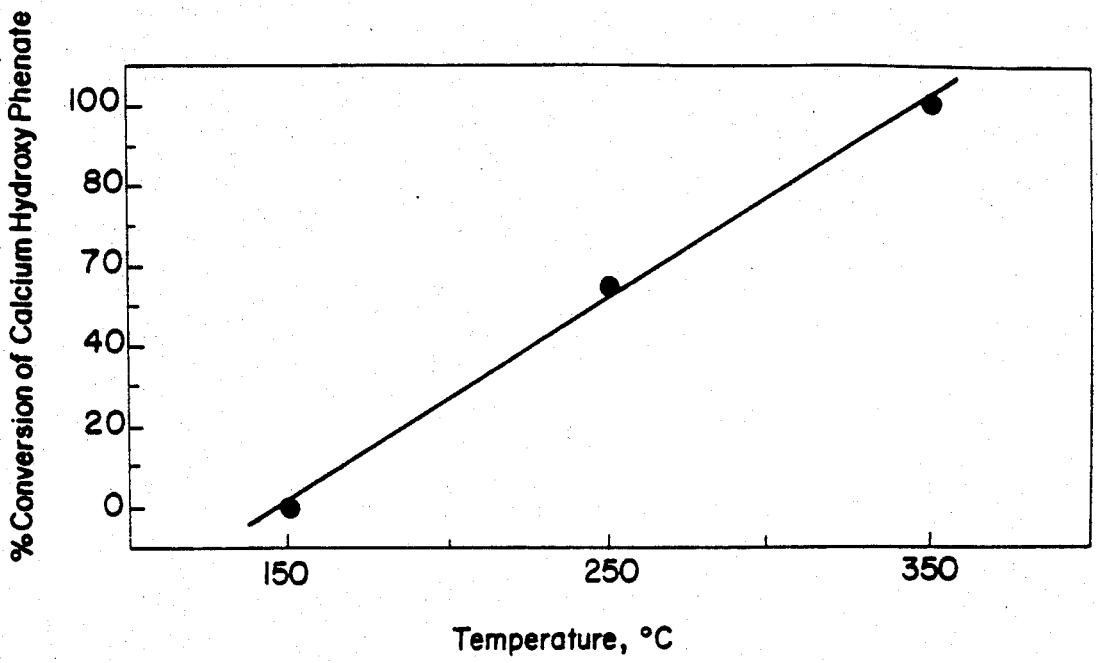
FIG. 1 is a plot of the amount of phenols recovered from calcium hydroxy phenate at various temperatures for a given period of time and at a molar ratio of water to calcium hydroxy phenate of 12 to 1.

Any solid metal phenate may be treated in accordance with the present invention for the recovery of phenols. Preferred phenates are those wherein the metal is selected from the alkali and alkaline-earth metals, more preferably the alkali metals sodium and potassium, and the alkaline-earth metal calcium.

It is not critical how the solid metal phenates are produced. They may result from a process for removing phenols from phenol-containing streams by treating the stream with one or more metal oxides or hydroxides which are capable of forming a metal phenate with the phenols of the stream.

In such a process, oxides and hydroxides of both monovalent metals, preferably the alkali metals, sodium and potassium; and multivalent metals, such as the alkaline-earth metals, are suitable, as long as they are capable of forming metal phenates with the phenaols of the treated stream. The choice of the one or more metal oxides or hydroxides employed is dependent on such factors as the desired final level of phenols-content of the stream, the reactivity of the particular phenol compounds to the metal, and the type of phenol one wishes to separate. For example, multivalent metal oxides and hydroxides are more reactive with the less sterically hindered phenols and therefore can be used to selectively remove such phenols, leaving most of the more sterically hindered phenols in the stream. On the other hand, oxides and hydroxides of monovalent metals, such as the alkali metals, will remove phenols with little preference to steric factors. Consequently, if a stream contains both sterically hindered and non-hindered phenols, and if it is predetermined to remove substantially all of the phenols regardless of steric hindrance, then an oxide and/or hydroxide of an alkali metal would be employed. For purposes herein, the term, metal phenates, also include hydroxy metal phenates.

The metal phenate which results from such a process is then separated from the stream and treated to remove any entrained material. This can be accomplished by filtration followed by washing, then followed by evaporation. This assures that the phenate will be free of nonphenolic material.

If it is necessary to measure the concentration of phenols, they can be measured by conventional analytical methods such as non-aqueous titration. The amount of multivalent metal needed to remove a predetermined amount of phenols can be expressed as the mol ratio of metal to phenolic-oxygen needed herein is that ratio which, when the metal oxides and/or hydroxides are contacted with the stream, will assure the removal of at least about 15 wt.% of the phenols from the feed stream at a temperature of about 25° C. for a contact time of about 90 minutes. The wt.% of phenol removal is based on the total weight of phenols in the stream.

It will be noted that because the activity of some metals is greater than that of other metals under a given set of conditions, less of the more active metal, for a given amount of phenols in the stream, will be required to remove a predetermined amount of the phenols from the stream. The relative activity of one metal to another is known in the art and the ratio of any given metal to oxygen can be determined by either routine experimentation or calculation by one having ordinary skill in the art.

It is believed that the following reactions occur when solid hydroxy metal phenates, and solid metal phenates are reacted with steam at a temperature of about 350° C., where Ar is an aryl- or hetero-aryl group.

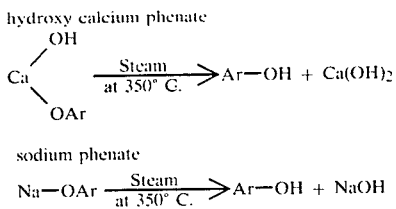

The above reactions show that phenates from both monovalent metals and multivalent metals are capable of producing the phenols and a metal hydroxide when treated with steam at temperature of about 350° C.

In the practice of the present invention, the metal phenate is treated with steam at a temperature from about 250° C. to 450° C., preferably from about 350° C. to 450° C. for an effective amount of time, thereby generating phenols as well as metal hydroxides. The phenols are collected and the metal hydroxides are recycled to the hydrocarbonaceous feed stream. Of course, multistage processing can be performed until the desired level of phenol removal is achieved.

The following examples serve to more fully describe the present invention. It is understood that these examples in no way serve to limit the true scope of this invention, but rather, are presented for illustrative purposes.

The metal phenates in the following examples were handled under an inert atmosphere of either helium or nitrogen to exclude both carbon dioxide and extraneous water. All transfers were carried out under nitrogen in a glove box. A small positive pressure of nitrogen gas was maintained during methylation reactions using a mineral oil bubbler as a pressure relief.

COMPARATIVE EXAMPLE A 1.30 g of calcium hydroxy phenate was placed in the reactor tube in a glove box under nitrogen. The reactor tube was connected to the preheater, capped, removed from the glove box, and installed in the furnace. A flow of helium sweep gas (100 ml/min.) was established and the accumulator was attached to the reactor tube. The preheater was heated to 250° C. and the reactor tube was heated to, and maintained at, 350° C. for 80 minutes, after which, it was cooled to room temperature under a flow of helium. The accumulator section was found to be empty. The reactor was capped and returned to the glove box where the residue was transferred to a reaction flask and methylated with 3.0 ml of iodomethane in 15 ml of N,N-dimethylformamide (DMF) solvent for 30 minutes at 60° C. to convert phenol moieties to anisole. Gas chromatographic analysis revealed that essentially all of the phenol moieties (99%) remained in the residue. Therefore, the calcium hydroxy phenate was thermally stable at 350° C., in the absence of steam, and did not release any phenols.

EXAMPLE 1

The procedure of Comparative Example A above was followed except that calcium hydroxy phenate was contacted with steam which was generated by feeding 1.87 ml of water into the preheater which was maintained at 250° C. This amount of water represented a 12 to 1 molar ratio of water to calcium hydroxy phenate and was fed to the preheater over a period of 10 minutes. The reactor tube was maintained at a temperature of 350° C. during the period of steam generation as well as for an additional 30 minutes to insure complete removal of volatiles from the residue. The reactor was then cooled, capped, and returned to the glove box. The methylation procedure of Comparative Example F was carried out on the residue. No anisole was detected in the product, hence, complete phenol liberation was obtained by steam stripping at 350° C. Analysis of the liquids in the accumulator by gas chromatography indicated a quantitative recovery of phenols from the calcium hydroxy phenate sample.

EXAMPLE 2 AND COMPARATIVE EXAMPLE B

The procedure of Example 19 above was followed except the temperature of the reactor tube was 150° C. for Comparative Example G and 250° C. for Example 20.

After steam stripping the phenate sample at 250° C., analysis of the residue and liquid indicated that 46% of the phenol moieties remained in the phenate residue while 54% were recovered as phenol.

After steam stripping the phenate sample at 150° C., analysis of the residue and liquid indicated that substantially all of the phenol moieties remained in the residue, while only a trace (<2%) were recovered as phenol.

The results of these two examples in combination with Example 19 above, in which steam stripping was carried out at a temperature of 350° C., illustrate that predetermined amounts of phenol can be recovered from a metal phenate by steam stripping the phenate at various temperatures for a given period of time and molar ratio of water to phenate.

The data of Examples 1, 2 and Comparative Example B are illustrated in FIG. 1 thereof.

EXAMPLES 3 AND 4

The procedure for Example 1 above was followed except the molar ratio of water to calcium hydroxy phenate was 4 to 1 for Example 4, and 9 to 1 for Example 3.

After steam stripping the phenate sample at 350° C. and molar ratio of water to phenate of 9 to 1, analysis of the residue and liquid indicated that approximately 75 wt.% of the phenol was recovered.

At a molar ratio of 4 to 1, approximately 35 wt.% of the phenol was recovered.

Thus, by adjusting the molar ratio of water to phenate in the steam stripping of a metal phenate at a given temperature and time period, one is able to recover a predetermined amoutn of phenol from the phenate.

Table I below sets forth the results of the above examples.

TABLE I

| | Wt. % Phenol Recovered From Calcium Hydroxy Phenate By Steam Stripping | | |
|---|---|---|---|
| Example | Temp °C. | Mol Ratio $H_2O$ to Phenate | Time in Minutes | Wt. % Phenol Recovered |
| F | 350 | No $H_2O$ | 80 | 0 |
| 19 | 350 | 12:1 | 10 | 100 |
| 20 | 250 | 12:1 | 10 | 54 |
| G | 150 | 12:1 | 10 | <2 |
| 21 | 350 | 9:1 | 10 | 75 |
| 22 | 350 | 4:1 | 10 | 35 |

Figure 2:
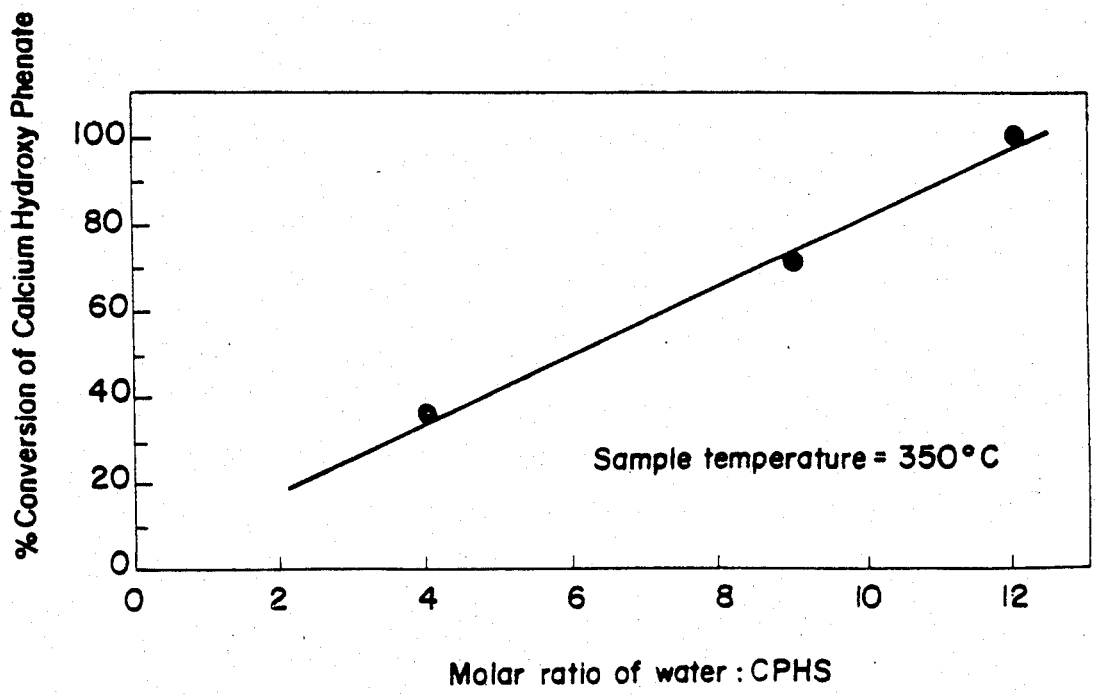
FIG. 2 illustrates that at a given temperature, such as about 350° C., and in a given period of time, various amounts of phenols can be recovered from calcium hydroxy phenate by adjusting the molar ratio of water to calcium hydroxy phenate.

The data of this table are also shown in FIG. 2 hereof.

COMPARATIVE EXAMPLE C AND D

The procedure of Comparative Example A above was followed except for Comparative Example C, 1.30 g of sodium phenate was employed; and, for Comparative Example D, 1.30 g of potassium phenate was employed. Analysis of the residue from both of these examples indicated that no phenol was liberated and no liquid was found in the accumulator.

EXAMPLES 5 AND 6

The experimental procedure of Example 1 above was followed except that for Example 23 1.30 g of sodium phenate was employed and for Example 24 1.35 g of potassium phenate was employed. Analysis of the residue and liquid from each example revealed that 85 wt.% of phenol was recovered from sodium phenate and 86 wt.% of phenol was recovered from potassium phenate.

What is claimed is:

1. A process for recovering phenols from solid metal phenates, which process comprises treating the solid metal phenates with steam at a temperature from about 250° C. to about 450° C. thereby forming phenols and hydroxides of the metal of the phenate.

2. The process of claim 1 wherein the metal of the phenates are selected from the phenates are selected from the alkali and alkaline-earth metals.

3. The process of claim 2 wherein the solid metal phenates are treated with steam at a temperature of about 350° C.

4. The process of claim 2 wherein the metal is selected from sodium, potassium, and calcium.

5. The process of claim 4 wherein the phenate is contacted with steam at a molar ratio of steam to phenate of at least about 10 to 1 and at a temperature of about 300° C. to about 350° C.

* * * * *